(12) United States Patent
Zimmerman et al.

(10) Patent No.: US 7,282,047 B2
(45) Date of Patent: Oct. 16, 2007

(54) MOVING ENERGY SOURCE

(75) Inventors: Yotam Zimmerman, Hadera (IL);
Boris Vaynberg, Zichron Ya'akov (IL);
Gal Aharonowitz, Gan-Haim (IL);
Yoni Iger, Haifa (IL)

(73) Assignee: Lumenis Ltd., Yokneam (IL)

( * ) Notice: Subject to any disclaimer, the term of this patent is extended or adjusted under 35 U.S.C. 154(b) by 384 days.

(21) Appl. No.: 10/357,496

(22) Filed: Feb. 4, 2003

(65) Prior Publication Data

US 2004/0152943 A1   Aug. 5, 2004

(51) Int. Cl.
*A61B 18/18*   (2006.01)

(52) U.S. Cl. .............................. 606/10; 606/9; 606/12; 606/131

(58) Field of Classification Search ............ 606/4, 606/5, 9–13, 131; 607/88, 89; 362/272–279
See application file for complete search history.

(56) References Cited

U.S. PATENT DOCUMENTS

| | | | | |
|---|---|---|---|---|
| 2,897,141 A | * | 7/1959 | Schocket | .................... 208/209 |
| 4,593,189 A | * | 6/1986 | Stoub | ......................... 250/221 |
| 4,930,504 A | * | 6/1990 | Diamantopoulos et al. | ... 607/88 |
| 5,938,657 A | * | 8/1999 | Assa et al. | ...................... 606/9 |
| 5,968,033 A | * | 10/1999 | Fuller et al. | .................... 606/9 |
| 5,971,976 A | * | 10/1999 | Wang et al. | ................... 606/1 |
| 5,980,513 A | * | 11/1999 | Frey et al. | ..................... 606/10 |
| 6,090,100 A | * | 7/2000 | Hohla | ............................. 606/5 |
| 6,328,458 B1 | * | 12/2001 | Bell et al. | .................... 362/371 |
| 6,406,474 B1 | * | 6/2002 | Neuberger et al. | ............. 606/9 |
| 6,569,155 B1 | | 5/2003 | Connors et al. | |
| 6,835,202 B2 | * | 12/2004 | Harth et al. | ................... 607/91 |
| 6,949,747 B2 | * | 9/2005 | Stark et al. | ............ 250/363.08 |

\* cited by examiner

*Primary Examiner*—A. Farah
(74) *Attorney, Agent, or Firm*—Pearl Cohen Zedek Latzer, LLP

(57) ABSTRACT

A device for moving a therapeutic energy source over an area to be treated including at least one therapeutic energy source adapted to produce therapeutic energy and coupled to a mounting structure, and at least one moving unit connected to the mounting structure and adapted to move the mounting structure and the energy source coupled thereto over an area to be exposed to therapeutic energy.

20 Claims, 4 Drawing Sheets

MOVING ENERGY SOURCE

FIELD OF THE INVENTION

The present invention relates in general to energy based medical and aesthetic devices. More specifically, the present invention relates to a system, a device, and a method of moving an energy source over a surface to be treated, and to a method of substantially inhibiting hair growth.

BACKGROUND

Energy based therapeutic devices are known to use an energy source to produce therapeutic energy to be delivered onto a surface to be treated. For example, it is known to use laser diode bars to produce electromagnetic energy of light at certain spectrum band for the treatment of a variety of medical and aesthetic conditions. Due to the small spot size of each diode bar it is considered impractical to use a single diode bar for treating an area that is larger than a few square millimeters. In order to provide an efficient treatment over large area, it is desirable to use more than one unit of diode bar. Current diode bar based therapeutic devices utilize a substantially large number of tens of laser diode bars (in the order of 20-140) bundled together to produce light for the treatment of much larger areas in comparison to that which may be treated when using only a single diode bar. Typically, all the diode bars in the bundle are simultaneously activated for a short period of time, such that an area that is substantially the size of the spot produced by the combination of the diode bars in the bundle is treated during each such activation session.

The inclusion of a large number of diode bars in each therapeutic treatment device is both costly and inefficient due to the high cost of each bar and due to the partial time during which each diode is activated. In addition, the energy produced by a large number of diode bars bundled together is less suitable for performing some medical or aesthetic procedures or treatments. For instance, current devices may cause destruction of hair components and, cessation of hair growth mechanism, when only a delay of hair growth cycle might be desired.

It is therefore desirable to provide energy based therapeutic device that may efficiently utilize one or a substantially small number of energy sources to expose a substantially large area to therapeutic energy, enabling a much cheaper and more efficient alternative to achieve a desired effect. In addition, it is desirable to provide an energy based therapeutic device capable of affecting biological processes in a controlled manner.

SUMMARY OF THE INVENTION

Some embodiments of the present invention relate to an apparatus, a system, and a method of moving a therapeutic energy source over an area to be treated. According to some embodiments of the present invention, the therapeutic energy based device may include at least one therapeutic energy source adapted to produce therapeutic energy and coupled to a mounting structure, and at least one moving unit connected to the mounting structure and adapted to move the mounting structure and the energy source coupled thereto over an area to be exposed to therapeutic energy.

Further embodiments of the present invention relate to a method of substantially inhibiting hair growth. Some embodiments of the method may include applying to a treatment area electromagnetic energy having a wavelength that is within a specific range and a substantially small spot size, such that at least a portion of the hair bulge is substantially affected, and the dermal papilla is substantially unaffected.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following non limiting detailed description when read with the accompanied drawings in which:

Figure 1:
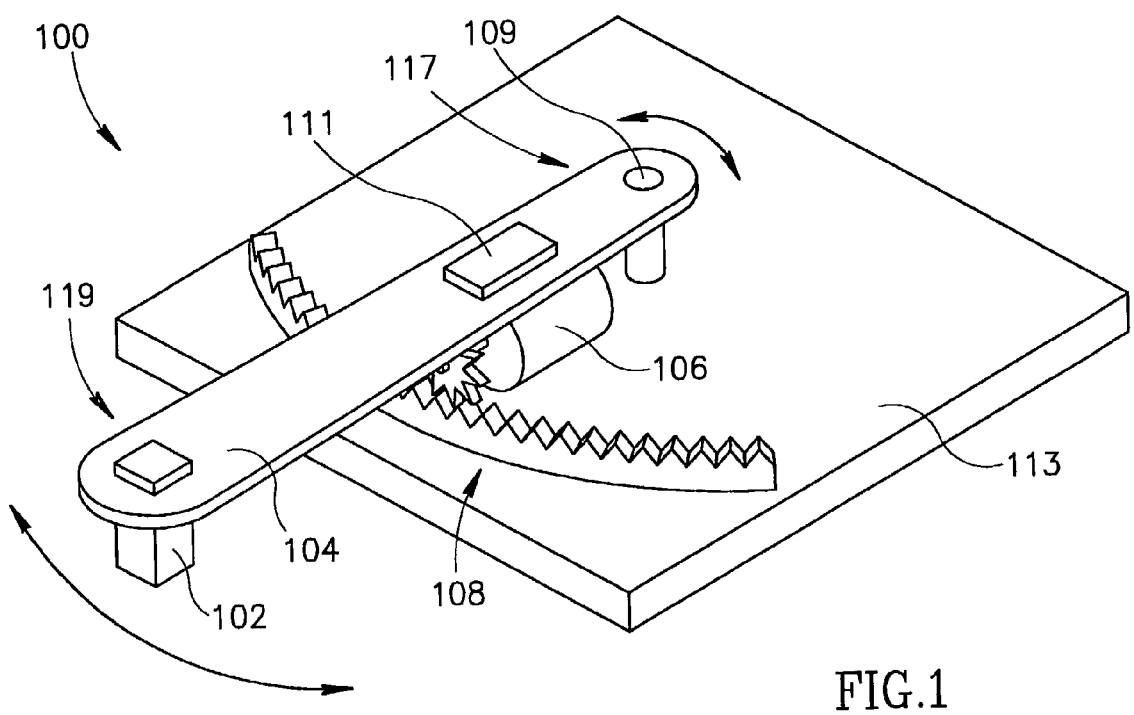
FIG. 1 is a block diagram illustration of a therapeutic energy based device for moving an energy source over an area to be exposed to therapeutic energy produced by the energy source, according to some embodiments of the present invention.

It will be appreciated that for simplicity and clarity of these non limiting illustrations, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods and procedures have not been., described in detail so as not to obscure the present invention.

Although the scope of the present invention is not limited in this respect, for the sake of clarity, some non limiting embodiments of the present invention may be directed towards methods of removing hair from a patient's body. Other non limiting embodiments of the present invention may be directed towards methods of inhibiting the growth of hair. Yet further embodiments of the present invention may be directed towards other aesthetic or medical procedures. However, it would be obvious to those of ordinary skill in the art how to modify the methods described hereinbelow to devise methods of treating a variety of additional aesthetic or medical conditions.

Although the scope of the present invention is not limited in this respect, for the sake of clarity, some embodiments of the present invention may be directed towards a therapeutic energy based device for moving an energy source including a diode laser bar over an area to be treated. However, it would be obvious to those of ordinary skills in the art that other therapeutic energy sources, capable of producing other forms of energy in a variety of wavelengths, may be used to perform a variety of procedures and treatments in a variety of fields, including but not limited to aesthetic or medical procedures.

Unless specifically stated otherwise, as apparent from the following discussions, it is appreciated that throughout the specification discussions utilizing terms such as "vertically", "horizontally", "up and down", "side to side", or the like, refer to imaginary axis substantially corresponding to a motion vectors of one or more elements of the device or of the system according to some embodiments of the present invention.

Reference now is made to FIG. 1, which is an illustration of a therapeutic energy based device for moving an energy source over an area to be treated, according to some embodiments of the present invention. The device 100 may include at least one energy source 102 and a moving unit 106. The device may also include a mounting structure 104. The energy source 102 may be coupled to the mounting structure 104. The moving unit 106 may be connected to the mounting structure 104. The moving unit 106 may be adapted to produce motion to enable the movement of the mounting structure 104 and of the energy source 102 coupled thereto.

According to some embodiments of the present invention the mounting structure 104 may be adapted to carry the therapeutic energy source 102 and to enable the movement of the therapeutic energy source 102 over the area to be exposed to therapeutic energy. For example, the mounting structure 104 may include a mounting arm. The mounting structure 104 may be used to couple the energy source 102 to one or more elements of the moving unit 106 such that the mounting structure 104 in cooperation with moving unit 106 may provide support to the therapeutic energy source 102 and may enable the energy source 102 to move over the area to be exposed to therapeutic energy. For example, the mounting structure 104 may include screws, bolts, adhesive materials, couplers, and other elements that may be suitable for coupling the energy source 102.

According to some embodiments of the device of the present invention, the energy source 102 may include at least one electromagnetic energy source. The energy source 102 may be adapted to produce electromagnetic energy. For example, the energy source 102 may be configured to produce electromagnetic energy having a substantially small spot size. In another example, the energy source may be adapted to produce light having a predetermined wavelength or range of wavelengths. The energy source 102 may include a diode laser or a diode laser bar. Other electromagnetic energy sources 102 may be used, including but not limited to, unipolar or bipolar RF electrodes, a light bulb, a laser, a microwave generator and/or other suitable energy sources. The energy source may be adapted to produce therapeutic energy having preselected characteristics, including but not limited to, a specific wavelength or spectra, a specific spot size, a specific modulation. The characteristics of the energy produced by the energy source 102 may be preselected or may be adjusted in accordance with predefined treatment conditions or other treatment parameters. According to further embodiments of the device of the present invention, the energy source 102 may include two or more distinct energy sources. The two or more energy sources may be cooperatively or independently operated.

According to one embodiment of the present invention, the energy source 102 may be activated in a certain modulation, including, but not limited to, various pulsed modes, to produce a variety of energy patterns. The energy source 102 may also be operated in a continuous mode to produce a substantially continuous energy output. The energy source 102 maybe activated in the continuous mode during the movement of the energy source 102 over an area to be treated, or in a certain sequence with the movement of the energy source 102, for instance immediately prior to or immediately after the commencement of the movement of the energy source 102. Thus, the area that may be exposed to energy produced by the energy source 102 may be substantially larger than the spot size of the energy source 102. When the energy source 102 is moved at a substantially constant speed over the area to be treated, and the energy source 102 is activated in the continuous mode during movement, the energy source 102 may deliver a substantially even dose of energy over the treatment area.

According to some embodiments of the present invention, the moving unit 106 may include an electric motor, such as a cyclic electric motor. Other embodiments of the device of the present invention may include other suitable moving units 106, for instance a magnetic motor, a manually operated moving unit motor or any other suitable moving unit. As part of some embodiments of the present invention the device 100 may also include a battery (not shown) or any other portable energy source to provide power to the moving unit 106 and to other elements or components of the device 100.

In the embodiment shown, the device 100 may further include a gear assembly 108. The gear assembly 108 may enable the transfer of motion from the moving unit 106 to the mounting structure 104. The gear assembly 108 may include a variety of gears and gear elements or combinations of such gears and gear elements to enable the transfer of the motion produced by the moving unit 106 to the mounting structure 104. The gear assembly 108 may be configured to modify certain aspects or parameters of the motion produced by the moving unit 106 prior to delivery of that motion to the mounting structure 104. Such modifications may include, but are not limited to, the modification of the velocity of the motion of the produced by the moving unit 106, the modification of the direction of the motion produced by the moving unit 106, and other aspects or parameters associated with the motion produced by the moving unit 106. For example, the gear assembly 108 may be configured to modify the direction of the motion produced by a cyclic motor in a manner to enable the mounting structure 104 to move substantially linearly.

It should be noted that the gear assembly 108 may be nonessential for the operation of some embodiments of the device of the present invention. Furthermore, in some embodiments of the device of the present invention the moving unit 106 may be directly engagable with the mounting structure 104 and the gear assembly 108 may be omitted.

According to further embodiments of the preset invention, the device 100 may further include one or more controllers 111. The controller 111 may include a Digital Signal Processor (DSP) unit either with or without specific software. The controller 111 may be adapted to control various aspect or parameters associated with the operation of one or more elements of the device 100. The controller 111 may be configured to modify various aspects of the operation of the device 100 and any of its elements in accordance with the operation parameters of one or more of the elements associated with the operation of the device 100. According to some embodiments of the preset invention, the device 100 may include two or more controllers 111. Each controller 111 may be adapted to control only part of the operation of the device 100. Each of two or more of the controllers 111 may be cooperatively operated to control one or more aspects of the operation of the device 100. Other controller 111 configurations may be used.

For example, the controller 111 may be adapted to substantially synchronize the dose, the fluence, and/or the modulation, of energy produced by the energy source 102 with the velocity or with any other parameter of the motion produced by the moving unit 106. Thus, the controller 111 may enable the energy source 102 to deliver a substantially even dose of energy over the area to be treated, independent of variations in the velocity of the motion produced by the moving unit 106 and any other variations associated with the operation of the device 100. The controller 111 may be adapted to control other aspects or parameters associated with the operation of the moving unit 106 and/or with the operation of gear assembly 108 and/or with the operation of the energy source 102. Those of ordinary skill in the art may appreciate that the synchronization between some aspects and/or parameters of the operation of two or more elements of the device 100 may allow substantial flexibility in the operation of the device 100, and may allow the operation of the device 100 in accordance with a variety of operation needs.

According to some embodiments of the present invention, the mounting structure 104 may include a mounting arm capable of carrying the energy source 102. The mounting structure 104 may be movable, thereby causing the therapeutic energy source 102 coupled thereto to move over an area to be exposed to therapeutic energy produced by the energy source 102. As part of some embodiments of the present invention, the device 100 may include at least one motion guides 109 to guide the movement of the mounting structure 104 in a desirable direction or directions. The at least one motion guide 109 may include linear guides, bearings, screws and other suitable motion guides or combinations of such motion guides. The motion guides 109 may be cooperatively operated with the controller 111. For example, the motion guides 109 may be adapted to guide the movement of the motion of the mounting structure 104 in a desired direction upon receiving an appropriate signal from the controller 111. At least one motion guide 109 may be positioned at a preselected location in relation to the moving unit 106 and the energy source 102, however other suitable locations may be selected. The motion guides 109 may also be connected to a substantially stationary surface or surfaces 113. The position of the motion guides 109 may be dynamically adjusted during the operation of the device 100, thereby enabling the modification of the motion pattern of the mounting structure 104, or of the energy source 102 per se.

In the embodiment shown in FIG. 1, the motion guides 109 may include a bearing. The bearing may be coupled to the proximal portion 117 of the mounting structure 104, and the energy source 102 may be coupled to distal portion 119 of the mounting structure 104. The bearing may also be coupled to a stationary surface 113, such that the mounting structure 104 may be capable of revolving around the bearing. The energy source 102, being, for example, a diode bar, may be positioned with its long axis perpendicularly to the plane of movement of the mounting structure 104, to enable larger area coverage during the movement of the mounting structure 104. When the mounting structure is in motion, the bearing may cause the mounting structure 104 to revolve around the bearing, thereby causing the energy source 102 to move in a wide arc motion.

Figure 2:
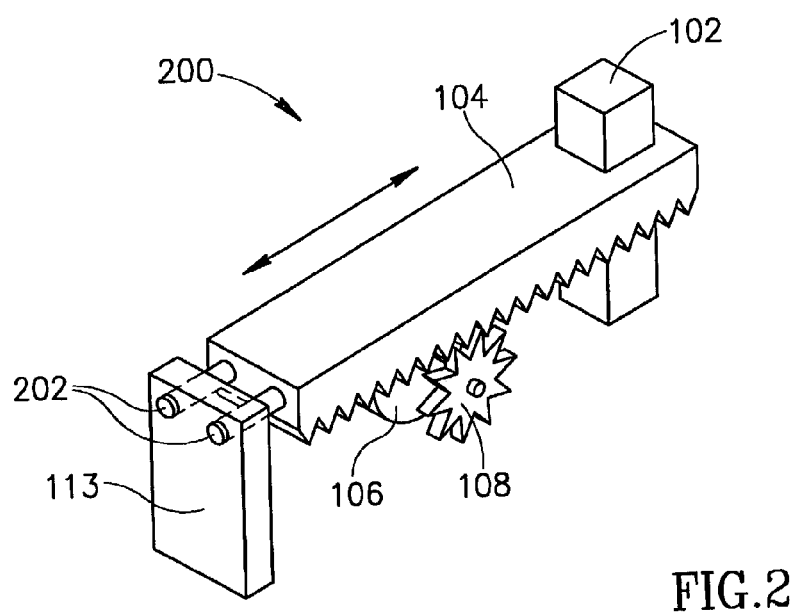
FIG. 2 is a block diagram illustration of a therapeutic energy based device for moving an energy source over an area to be exposed to therapeutic energy produced by the energy source, including a linear guide, in accordance with some embodiments of the present invention.

Reference is now made to FIG. 2 which is an illustration of a therapeutic energy based device for moving an energy source over an area to be treated, and including a linear guide according to some embodiments of the present invention. In the embodiment shown the device 200 may further include at least one linear guide 202. The linear guide 202 may be coupled to the mounting structure 104. The linear guide 202 may also be connected to a stationary surface 113. The linear guide 202 may permit the mounting structure 104 to move substantially linearly, horizontally from side to side or vertically back and forth. The linear guide 202 may also be adapted to prevent the mounting structure 104 from moving in any other direction.

Accordingly, when the moving unit 106 is activated the gear assembly 108 may deliver movement to the mounting structure 104, thereby causing the mounting structure 104 and the energy source 102 connected thereto, to move. The direction of the movement delivered by the gear assembly 108 to the mounting structure 104 may substantially correspond to the motion vector that may be permitted by the linear guide 202, for example, vertically or horizontally. Thus, when the moving unit 106 is activated, the gear assembly 108 may cause the mounting structure 104 to move and the linear guide 202 may ensure that the mounting structure 104 can move only in the desired direction. The possibility of predetermining the movement pattern of the mounting structure 104 and of the energy source 102 coupled thereto, may enable to predetermine the movement of the energy source 102 over the area to be exposed to therapeutic energy produced by the energy source 102.

Those of ordinary skill in the art may appreciate that some embodiments of the device of the present invention may be configured to enable a two axis motion of the mounting structure 104 and of the energy source 102 coupled thereto, along a first axis and across a second axis. Some embodiments of the device 200 may be configured to enable a variety of two axis motion patterns. Any suitable two axis motion configurations known in the art or yet to be devised in the future may be used to enable the mounting structure 104 and the energy source, 102 coupled thereto to move in a desirable two dimensional motion pattern. For example, the embodiments shown in FIG. 1 and FIG. 2 described above may be combined with minor modifications to provide a device that may enable the energy source to move along a first axis and across second axis over an area to be treated.

Figure 3:
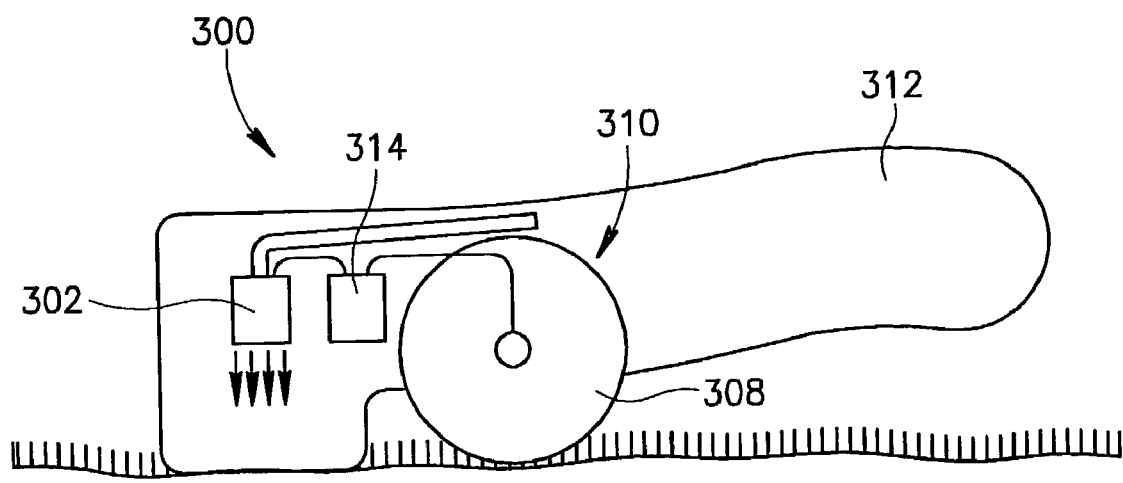
FIG. 3 is a block diagram illustration of an energy based therapeutic device for moving an energy source over an area to be exposed to therapeutic energy produced by the energy source, including a high friction encoder wheel, in accordance with some embodiments of the present invention.

Reference is made now to FIG. 3, which is an illustration of an electromagnetic therapeutic device for moving an energy source over an area to be treated including a decoder according to some embodiments of the present invention. In the embodiment shown, the device 300 may include a decoder 308. The decoder 308 may include a high friction decoder wheel 310. According to some embodiments of the present invention, the decoder wheel 310 and the energy source 302 may be coupled to a supportive structure 312. According to one embodiment of the present invention the supportive structure 312 may be a frame of a handpiece. The decoder wheel 310 may be adapted to rotate when force is applied to it, for example when the decoder wheel 310 is pushed or pulled. The decoder 308 may be adapted to monitor the motion of the decoder wheel 310. The decoder 308 may be adapted to translate the motion of the decoder wheel 310 to signals, for instance mechanic, magnetic, electronic signals or any other suitable signal.

In the embodiment shown, the moving unit (not shown) may not be incorporated into the energy based device 300, and the force from an exterior source, such as an exterior motor, may be applied to the decoder wheel 310 causing the decoder wheel 310 to rotate. For example, the supportive structure 312, together with the decoder wheel 310 and the energy source 302 coupled thereto, may be pushed by a user in a substantially forward motion over a surface to be treated, thereby causing the decoder wheel 310 to rotate and the energy source 302 to move over the area to be treated.

The decoder 308, either alone or in combination with a controller 314, may be adapted to synchronize certain aspects, and/or parameters of the operation of one or more elements associated with the operation of the device 300. For example, the decoder 308, either alone or in combination with a controller 314, may be adapted to synchronize the amount, the modulation, and/or the pulse duration of energy produced by the energy source 302 according to the velocity of the rotation of the decoder wheel 310. Thus, during the movement of the supportive structure 312, together with the decoder 308 and the energy source 302 coupled thereto over the area to be treated, the decoder 308, either alone or in combination with the controller 314, may modify the amount of energy produced by energy source 302, for example, upon detecting a variation in the speed of the decoder wheel 310.

Certain aspects associated with the movement of the energy source 302 may be inferred from the movement of the decoder wheel 310. The decoder 308, either alone or in combination with the controller 314, may cause the energy source 302 to shift towards a continuous mode, in accordance with the velocity of the motion of the decoder wheel 310. The decoder 308, either alone or in combination with the controller 314, may also change, for instance, the pulse duration or the fluence of the energy produced by the energy source 302. Those of ordinary skill in the art may appreciate that as the velocity of decoder wheel 310 increases the decoder 308, either alone or in combination with the controller 314 may cause the energy source 302 to produce pulses of energy in decreasing intervals between the pulses, towards continuous mode of operation. For example, the decoder 308, either alone or in combination with the controller 314, may cause the energy source 302 to produce a pulse of energy for a duration of 100 ms, for each 0.2 mm of movement of the energy source. When the velocity of the movement of the decoder wheel 310 is equal to a predetermined threshold, the decoder 308, either alone or in combination with the controller 314 may enable the operation of the energy source 302 in a continuous mode to produce energy substantially continuously to affect the treatment area.

The decoder 308, either alone or in combination with the controller 314, may be configured to monitor the operation of other elements of the device 300 and may be adapted to modify these and other aspects or parameters associated with the operation of the device 300.

Figure 4A:
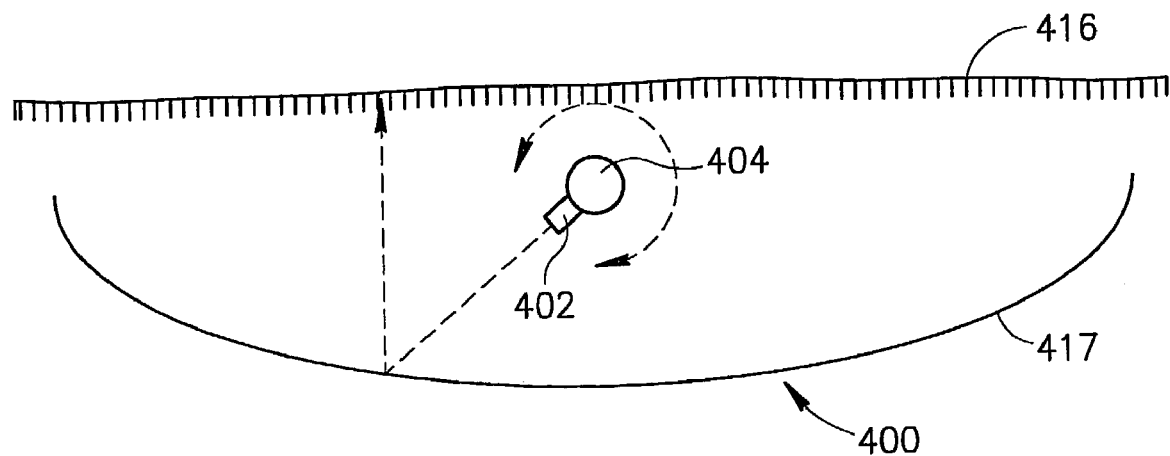
FIG. 4A is a view from above of a therapeutic energy based device for moving an energy source over an area to be exposed to therapeutic energy produced by the energy source, according to some embodiments of the present invention.
Figure 4B:
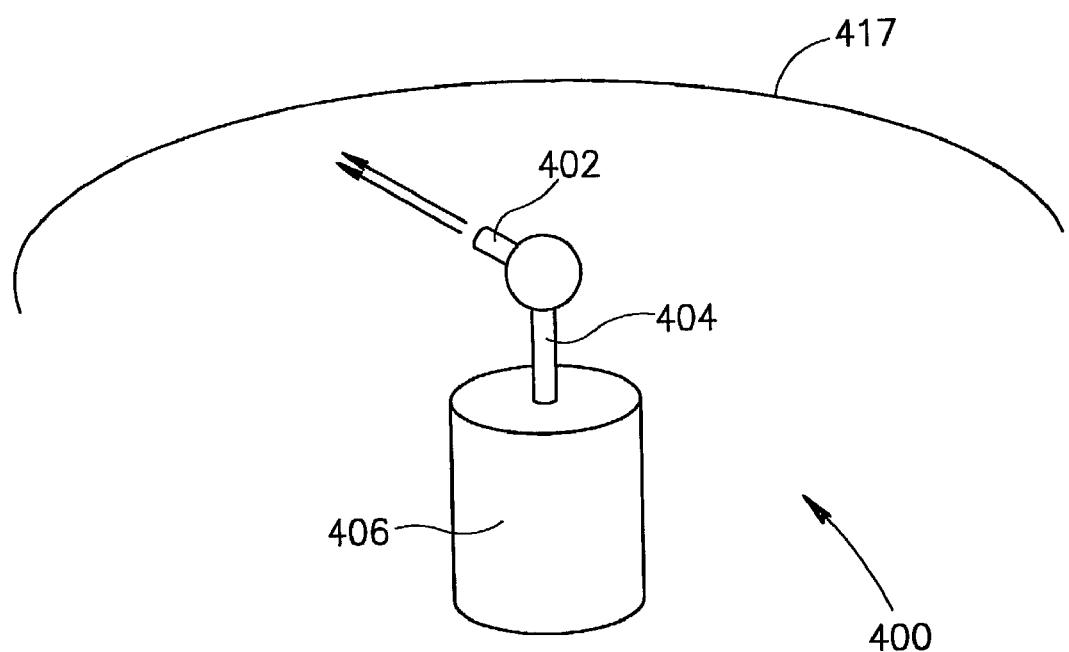
FIG. 4B is a block diagram illustration of a therapeutic energy based device for moving an energy source over an area to be exposed to therapeutic energy, according to some embodiments of the present invention.

Reference is now made to FIG. 4A, which is a view from above of a therapeutic energy based device for moving an energy source over an area to be exposed to therapeutic energy according to some embodiments of the present invention. In addition, reference is now made to FIG. 4B, which is an illustration of a therapeutic energy based device for moving an energy source over an area to be treated according to some embodiments of the present invention. The device 400 may include at least one energy source 402 and a moving unit 406. The energy source 402 may be coupled to the moving unit 406.

In the embodiment shown, the moving unit 406 may be a cyclic electric motor. One of the elements of the motor 406, such as the motor shaft, may be used as a mounting structure 404, to couple the moving unit 406 to the energy source 402. When the electric motor 406 is activated, the motor shaft 404 may turn, thereby causing the energy source 402 connected thereto to move in a substantially circular motion. It should be noted that the moving unit is not limited to cyclic motors and that other suitable moving units may be used, and also that other elements of the moving unit may be used to couple the energy source to the various moving elements.

According to some embodiments of the present invention, the device 400 may further include an energy adjuster 417. The energy adjuster 417 may be adapted to modify certain aspect or parameters of the energy produced by the energy source 402. In the embodiment shown, the energy adjuster 417 may be adapted to cancel-out the effects of a rotational movement, upon the energy produced by the energy source 402. For example, the energy adjuster 417 may include a spherical mirror to collimate to re-collimate or to diverge laser energy produced by a laser diode bar facing the curvature of the mirror when the laser diode bar is moving in a substantially cyclic motion. The spherical mirror may re-direct the electromagnetic energy to enable the exposure of each point within the area to be exposed 416 to a substantially even amount of energy. It should be noted that the energy adjuster 417 may include other elements to enable the modification of other aspect or parameters of the energy produced by the energy source 402.

The moving unit, the mounting arm, the at least one energy source and other elements described above may be combined in numerous other combinations and configurations to allow the energy source to move over an area to be exposed to therapeutic energy in a variety of movement patterns and movement configurations. It should be noted that the present invention is not limited to any such specific configurations. Rather, the present invention may be carried out using any suitable combination or combinations of one or more of the moving unit, the mounting arm, the at least one energy source.

Those of ordinary skill in the art may appreciate that some embodiments of the device or system of the present invention may be suitable for performing a variety of current or yet to be devised procedures in a variety of fields and for a variety of purposes, including but limited to aesthetic and/or medical treatments and procedures. For each of the treatments or procedures the device of the present invention may be operated in accordance with a unique set of parameters or in accordance with a specific operation protocol.

For example, hair removal requires the exposure throughout the area to be treated to energy fluence in the order of 15

J/cm². The spot size of the laser diode bar may be a=0.2 cm in width, and b=1 cm in length. Accordingly, the spot size of the laser diode may be 0.2 cm². The power that may be generated by the single diode bar may be in the order of 30 watts. Let us also assume that the energy source is continuously moved and activated for a period of 1 second. The dwelling time may be derived from tissue requirements. Those of ordinary skill in the art may appreciate that when the energy source of such exemplary device is operated in the continuous mode and is moved at a constant speed of 2 cm/sec, an energy fluence in the order of 15 Joule/cm² may be delivered substantially evenly to the area to be exposed to the therapeutic energy.

This may be mathematically illustrated as follows:

Where T denotes the exposure time, P denotes the laser power, A denotes the spot size of the diode laser and E denotes the energy fluence of the diode laser, the following relationship applies:

$$E = \frac{P \times T}{A} \quad (1)$$

The energy fluence of a device operated in accordance with the above parameters may therefore be calculated:

$$E = \frac{30 \times 0.1}{0.2} = 15 J/cm2 \quad (2)$$

The total area to be exposed to electromagnetic energy produced by the exemplary single moving diode bar device may be equal to the speed of the movement of the laser diode over the, area to be exposed, times the spot length, times the period of time during which the laser diode is activated and moved. If we consider the operation of the exemplary device in accordance with the above parameters, then the area to be exposed to electromagnetic energy produced by the laser diode is 2 cm².

The exemplary device, when operated in accordance with the operation parameters discussed above may produce an energy fluence that is similar to the energy fluence of current hair removal devices using multiple laser diode bars, with the difference that the diode of the present exemplary device may be operated substantially towards continuous mode during the period of time in which the diode bar is moved over the area to be treated, whereas current hair removal devices, utilize pulsed mode operation in which all the multiple diodes bundle are activated together for only a short period of time over the area to be treated.

Typically, for hair removal, the multiple diode bars may be activated for a period of about 0.1 second (100 ms), over an area, that is substantially equal to the combined spot size of the multiple laser diode bars, altogether in the order of 1-2 cm². Some embodiments of the device of the present invention may enable the exposure of the area to be treated to similar energy outputs using only a single diode bar (or a substantially small number of diodes) instead of a substantially large number of diode bars as in some of the current energy treatment devices.

Some embodiments of the device of the present invention may be configured in accordance with other current energy based treatment devices to enable the treatment of similar conditions or disorders including but not limited to substantially permanent hair removal, inhibition of hair growth cycle and others. Other embodiments of the device of the present invention may be used for carrying out a variety of procedures or treatments which have yet to be devised using current energy based treatment devices.

According to some embodiments of the present invention, there is provided a method of inhibiting hair growth. Some embodiments of the method of substantially inhibiting hair growth may include applying to a treatment area electromagnetic energy having a wavelength that is within a specific range and a substantially small spot size, such that at least a portion of the hair bulge is substantially affected, and the dermal papilla is substantially unaffected.

Those of ordinary skill in the art may appreciate that various aspects of the energy output produced by the energy source may influence the interaction of the energy with the tissue to be treated and the surrounding tissue. The use of electromagnetic energy having a wavelength that is within a specific wavelength range may promote a desirable effect on a targeted tissue located in predetermined tissue depths with a minimal effect on surrounding tissues.

The spot size of the electromagnetic energy may also affect the fluence of energy in the various skin depths. It is known that the spot size of electromagnetic energy applied to a tissue or tissues may affect the fluence of the energy in the tissue depths. One factor, which may be associated with this effect of the spot size of the energy upon the fluence of the energy in the tissue depths, may be the interaction of the energy components, such as photons, with each other and with the surrounding tissues. When the spot size of the energy output is substantially large the interaction of the particles with each other may be substantially widespread, and the effect of these interactions on the fluence of the energy in the tissue depth may be greater or more extensive. Consequently, deeper than a certain threshold depth, the smaller the spot size, the lower the fluence will be in tissues located below the threshold depth. The threshold depth may be associated with the spot size of the energy output. The exposure of the area to be treated to an energy output having a substantially small spot size may enable (together with a specific wavelength) the delivery of effective energy fluence up to only predetermined tissue depths. Thus, the absorption of the energy may be similarly limited to tissues located at these specific depths. Accordingly, the effect of the energy may be controlled such that only tissue components located at these specific tissue depths may be affected. The disruptive effect to other tissues located at deeper depths may thus be prevented.

Figure 5:
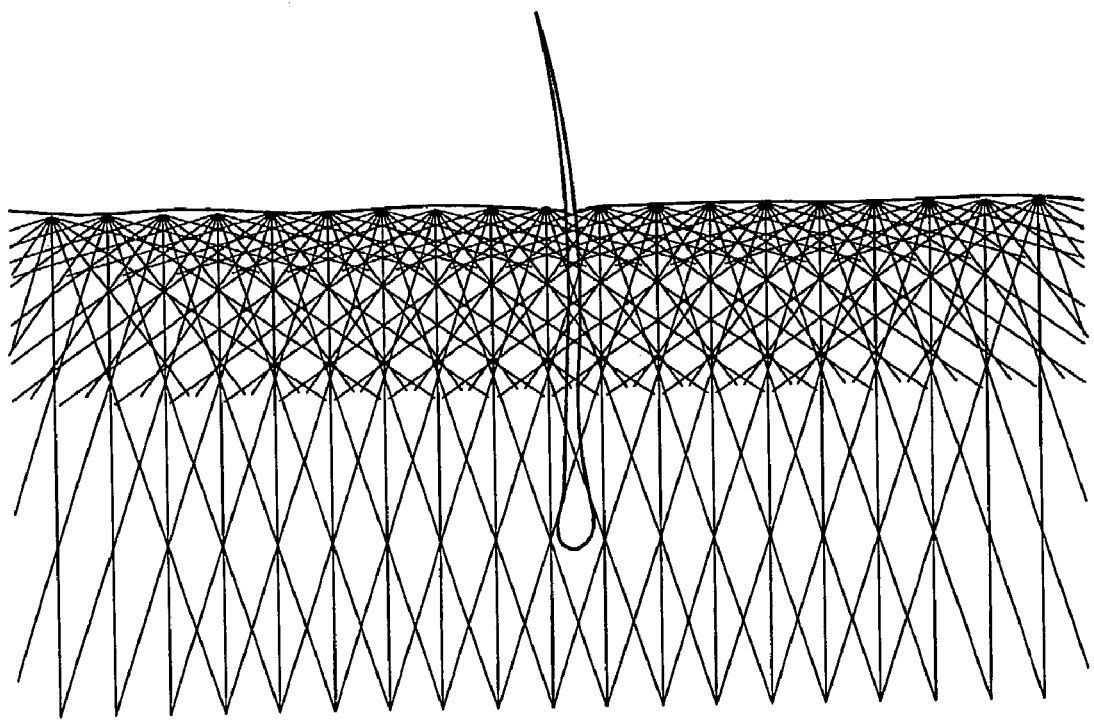
FIG. 5 is a schematic computer generated graphical illustration of the fluence of electromagnetic energy in various depths of the skin tissue, when the spot size of the energy applied to the skin is substantially large.
Figure 6:
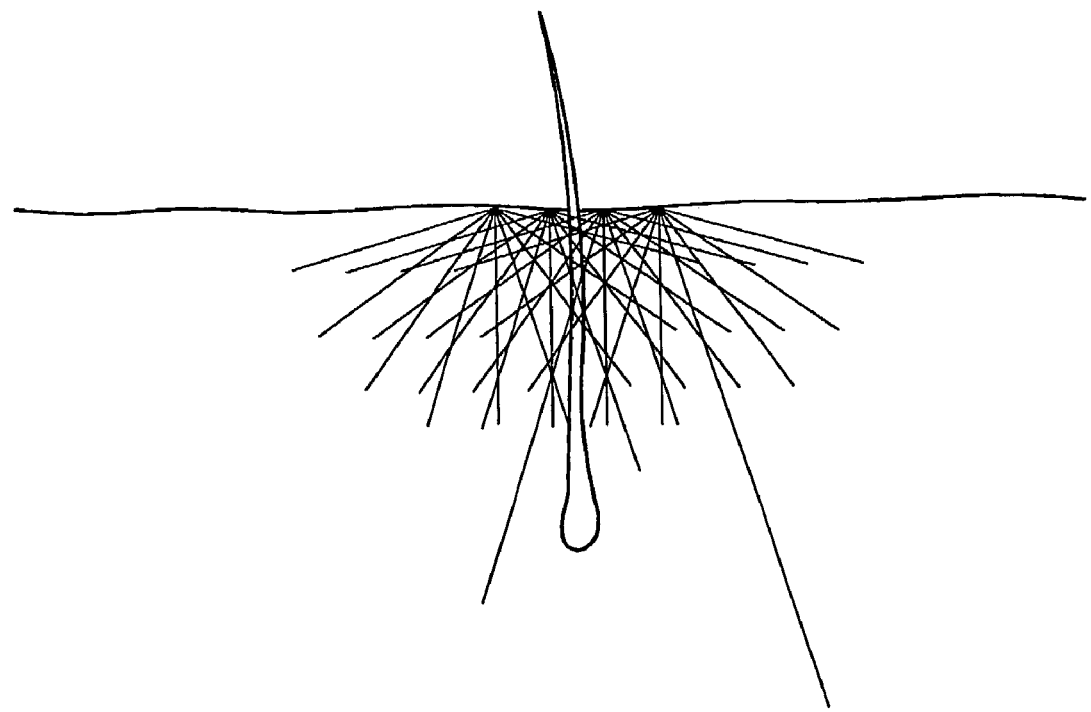
FIG. 6 is a schematic computer generated graphical illustration of the fluence of electromagnetic energy in various depths of the skin tissue, when the spot size of the energy applied to the skin is substantially small.

Reference is now made to FIG. 5, which is a schematic illustration of the fluence of electromagnetic energy in various depths of the skin tissue, when the spot size of the energy applied to the skin is substantially large, and to FIG. 6, which is a schematic illustration of the fluence of electromagnetic energy in various depths of the skin tissue, when the spot size of the energy applied to the skin is substantially small.

Thus, by controlling or by selecting the wavelength and the spot size of electromagnetic energy to be applied the treatment area, the fluence of the energy in the tissue depths may be controlled, such that at least a portion of the hair bulge may be substantially affected, and the dermal papilla may be substantially unaffected.

The specific wavelength or wavelength range and the spot size parameters may be selected in accordance-with the treatment conditions. The treatment conditions may include, but are not limited to, skin pigmentation, the length of the hair follicles (including bulge and bulb) in that specific body area, as well as other factors. Variations in some of the treatment conditions may affect the fluence of the electromagnetic energy in the tissue depths. By adjusting the wavelength of and/or the spot size of the electromagnetic energy the fluence of the energy in the tissue depths may be controlled, such that at least a portion of the hair bulge may be substantially affected, and the deeper dermal papilla may be substantially unaffected.

According to some embodiments of the present invention, the wavelength of the energy to be applied to the skin may be within the range of 500 nm-1100 nm, and the spot size may be up to 100 microns width by millimeters to tens of millimeters length. It should be noted that these ranges are non-limiting and that other wavelength or spot size parameters may also be suitable for substantially affecting at least a portion of the hair bulge while substantially unaffecting the dermal papilla. Furthermore, it should be noted that various treatment conditions, such as a specific hair follicle length (or depth), may dictate a more limited range of wavelengths and/or spot size parameters that may be suitable for substantially affecting at least a portion of the hair bulge while substantially unaffecting the dermal papilla.

According to one embodiment of the present invention, the wavelength of the energy to be applied to the treatment area may be within the range of 600 nm-900 nm and the spot size of the energy source may be in the order of 5 microns by millimeters. For example, under typical treatment conditions, when applying to the area to be treated electromagnetic energy having the above wavelength and spot size parameters, the fluence of the energy in the tissue depth of approximately 2 mm and deeper may be insufficient to substantially affect the tissue located at these depths, while the fluence of the energy in the tissue depth of up to approximately 1.5 mm under the surface of the skin may be sufficient to substantially affect tissue located at these depths. Thus, assuming that the at least a portion of the hair bulge is located at a depth of approximately 1.5 mm and that the dermal papilla, or bulb, is located deeper than a depth of 2 mm below the skin surface, at least a portion of the hair bulge may be substantially affected, and the dermal papilla may be substantially unaffected, when using the above wavelength and spot size parameters.

It should be noted that the above wavelength ranges and spot size dimensions are non-limiting and have been provided for illustrative purposes only, by being representative of the wavelength and spot size parameters of some of the current commercially available laser diode bars. Other wavelengths and/or spot size parameters may also allow selective thermolysis of tissues located at similar depths or depth ranges using a variety of electromagnetic energy sources.

Those of ordinary skill in the art may appreciate that a normal hair growth cycle of the human hair follicle may be maintained as long as the essential hair growth regions are active, i.e. as long as both the hair bulge region, typically located at the upper third of the hair follicle under the surface of the skin, and the dermal papillae region, typically located at the lower third of the hair follicle under the surface of the skin, are substantially intact. When both the hair bulge and the hair papilla are disabled, hair growth may be substantially permanently discontinued. When only one of essential hair growth regions is destroyed or substantially affected the growth cycle may be hampered or suspended. Accordingly, the destruction or otherwise disrupting of either the hair bulge or the hair papillae may lead to the suspension or otherwise hampering the normal hair growth cycle. However, often in case that only one of the essential hair growth regions (i.e. the hair bulge or the hair papillae) is destroyed or at least substantially affected, the growth cycle may not be altogether discontinued, and with time growth cycle restoration may occur. Thus, by controlling the distribution of the electromagnetic energy under the surface of the skin, for example, such that the energy at depth of up to a third of the length of the hair follicle (where the hair bulge is located) may be sufficient to substantially affect the tissues located at these depths, while the energy at a depth of two-thirds of the hair follicle and deeper (where the dermal papilla is located) may be insufficient to substantially affect the tissues located at these depths, it may be possible to destruct or otherwise disrupt the hair bulge while substantially unaffecting the dermal papilla, and to achieve hair growth cycle delay.

Thus by applying to the area to be treated electromagnetic energy having a wavelength that is within a specific range and a substantially small spot size, and by controlling or selecting the wavelength and the spot size parameters of the energy, such that at least a portion of the hair bulge is substantially affected, and the dermal papilla is substantially unaffected, the hair growth-cycle may be inhibited.

A variety of devices may be suitable carrying out the method of substantially inhibiting hair growth according to some embodiments of the present invention. For example, a device similar to the device illustrated in the embodiment shown in FIG. 1 may be used to produce energy having suitable wavelength and spot size parameters. In accordance with the device described with reference to FIG. 1, the energy source may be moved over the area to be treated. Accordingly, the area that may be exposed to energy produced by the energy source may be substantially larger than the spot size of the energy source, without compromising the wavelength and spot size parameters that may be required in order to achieve the selective thermolysis as discussed above. However, it should be noted that further embodiments of the present invention may be carried out using a variety of presently available or yet to be devised in the future energy based therapeutic devices. Such energy based therapeutic devices may include a variety of energy sources adapted to produce energy having suitable wavelength and spot size parameters that may be required in order to achieve the depth-related selective thermolysis and the inhibition of hair growth, as discussed above.

While certain features of the invention have been illustrated and described herein, many modifications, substitutions, changes, and equivalents may now occur to those of ordinary skill in the art. It is, therefore, to be understood that the appended claims are intended to cover all such modifications and changes as fall within the true spirit of the invention.

What we claim is:

1. A device for moving a therapeutic energy source over an area to be treated comprising:

a mounting structure;

at least one therapeutic energy source coupled to said mounting structure and adapted to produce therapeutic energy;

at least one moving unit operatively connected to said mounting structure and adapted to move said mounting structure and said energy source over the area to be treated by therapeutic energy;

a motion sensor to detect motion of said device with respect to said area to be treated; and a controller to control a treatment parameter based on said motion, wherein said controller comprises a rotational member and is adapted to synchronize said therapeutic energy source with the velocity of said rotation member, thereby controlling the dose of energy to be delivered to substantially each point within the area.

2. The device of claim 1, wherein said at least one therapeutic energy source comprises at least one electromagnetic energy source.

3. The device of claim 1, wherein said at least one therapeutic energy source comprises a single electromagnetic energy source.

4. The device of claim 3, wherein said single electromagnetic energy source is a laser diode bar.

5. The device of claim 1, wherein said therapeutic energy source is modulated to produce a predefined pulse pattern.

6. The device of claim 1, wherein said therapeutic energy source is configured to operate in a continuous mode to produce a substantially continuous energy output.

7. The device of claim 6, wherein said therapeutic energy source is activated in said continuous mode at least during a portion of the movement of said therapeutic energy source over the area to be exposed.

8. The device of claim 7, wherein said therapeutic energy source is moved at a substantially constant speed over the area to be exposed.

9. The device of claim 8, further comprising a gear assembly to deliver motion from said moving unit to said mounting structure and said therapeutic energy source coupled thereto.

10. The device of claim 9, wherein said gear assembly is adapted to modify one or more parameters of the movement of the moving unit.

11. The device of claim 7, wherein said moving unit is an electric motor.

12. The device of claim 7, wherein said moving unit is manually driven.

13. The device of claim 1, wherein said controller is adapted to control the dose of energy to be delivered to substantially each point within the area, such that said dose of energy is within a predetermined range.

14. The device of claim 13, wherein said controller is adapted to control the dose of energy to be delivered to substantially each point within the area, such that said dose of energy is substantially even.

15. The device of claim 1, wherein said at least one moving unit is adapted to move said mounting structure and said therapeutic energy source coupled thereto over a first axis and over a second axis of an area to be exposed to therapeutic energy.

16. The device of claim 1, wherein said at least one moving unit is adapted to move said mounting structure and said energy source coupled thereto relative to said device, and wherein to device is adapted to be moved over said area to be exposed during treatment.

17. A device for affecting an area substantially larger than the spot of the energy produced by a therapeutic energy source, comprising:
    a mounting structure;
    at least one therapeutic energy source adapted to produce therapeutic energy and coupled to a said mounting structure;
    at least one moving unit connected to said mounting structure and adapted to move said mounting structure and said therapeutic energy source over the area to be exposed to therapeutic energy; and
    a wheel operatively connected to said moving unit in contact with tissue proximate to the area, wherein movement of said wheel on said tissue controls at least one parameter of said energy source.

18. A device for moving a therapeutic energy source over an area to be treated comprising:
    at least one therapeutic energy source adapted to produce therapeutic energy;
    at least one moving unit, said moving unit is adapted to move the energy source over the area to be exposed to therapeutic energy;
    means for mounting said at least one therapeutic energy source onto said at least one moving unit; and
    a wheel operatively connected too said moving unit in contact with tissue proximate to said area, wherein movement of said wheel on said tissue controls at least one parameter of the energy source.

19. A method of affecting an area substantially larger than the spot of the energy produced by a therapeutic energy source, comprising:
    positioning at least one therapeutic energy source over a first portion of an area of a patient's body tissue;
    moving said at least one therapeutic energy source over a second portion of the area of the patient's body;
    activating said at least one therapeutic energy source during at least a portion of the movement of said therapeutic energy source over said second portion of the area of the patient's body; and
    controlling at least one parameter of said energy source according to monitored movement of a wheel on a tissue proximate to said area.

20. The method of claim 19, wherein said therapeutic energy source is contained in a device, wherein moving said at least one therapeutic energy source over at least a second portion of the area of the patient's body to be treated comprises moving said energy source relative to said device, and further comprising the step of moving said device relative to said second area to be treated.

* * * * *

UNITED STATES PATENT AND TRADEMARK OFFICE
CERTIFICATE OF CORRECTION

| | |
|---|---|
| PATENT NO. | : 7,282,047 B2 |
| APPLICATION NO. | : 10/357496 |
| DATED | : October 16, 2007 |
| INVENTOR(S) | : Yotam Zimmerman et al. |

It is certified that error appears in the above-identified patent and that said Letters Patent is hereby corrected as shown below:

In Claim 18, Column 14, Lines 25-28

"a wheel operatively connected too said moving unit in contact with tissue proximate to said area, wherein movement of said wheel on said tissue controls at least one parameter of the energy source."

should read

--a wheel operatively connected to said moving unit in contact with tissue proximate to said area, wherein movement of said wheel on said tissue controls at least one parameter of the energy source.--

Signed and Sealed this

Tenth Day of June, 2008

JON W. DUDAS
*Director of the United States Patent and Trademark Office*